United States Patent [19]

Gadient

[11] Patent Number: 4,478,750
[45] Date of Patent: Oct. 23, 1984

[54] 1-PHENYL-AZEPINOINDOLES

[75] Inventor: Fulvio Gadient, Birsfelden, Switzerland

[73] Assignee: Sandoz Ltd., Basel, Switzerland

[21] Appl. No.: 385,867

[22] Filed: Jun. 7, 1982

Related U.S. Application Data

[63] Continuation of Ser. No. 201,251, Oct. 27, 1980, abandoned.

[30] Foreign Application Priority Data

Nov. 2, 1979 [CH]  Switzerland ......................... 9852/79

[51] Int. Cl.$^3$ .................... A61K 31/55; C07D 471/04; C07D 487/04
[52] U.S. Cl. .................................. 260/245.7; 424/274; 546/85; 546/86; 548/493; 548/504; 548/507
[58] Field of Search ...................... 260/245.7; 424/274

[56] References Cited

U.S. PATENT DOCUMENTS 3,419,569 12/1968 Renner ............................. 260/245.7
3,652,588  3/1972 Hester .............................. 260/245.7
3,839,357 10/1974 Hester ............................. 260/245.7

OTHER PUBLICATIONS

Arzneim. Forsch., vol. 32, pp. 853–860, (1982).

Primary Examiner—Alton D. Rollins
Attorney, Agent, or Firm—Gerald D. Sharkin; Robert S. Honor; Joseph J. Borovian

[57] ABSTRACT

A 1,2,3,4,5,6-hexahydro-6-phenyl-azepino[4,5-b]indole, or a pharmaceutically acceptable acid addition salt thereof is a useful neuroleptic, anti-depressant and anti-allergic agent.

7 Claims, No Drawings

1-PHENYL-AZEPINOINDOLES

This is a continuation of application Ser. No. 201,251 filed Oct. 27, 1980, now abandoned.

This invention relates to azepinoindoles, their production and pharmaceutical compositions containing them.

The present invention provides 1,2,3,4,5,6-hexahydro-6-phenyl-azepino[4,5-b]indoles or pharmaceutically acceptable acid addition salts thereof hereinafter referred to as compounds of the invention. It is to be appreciated that the compounds of the invention may be optionally substituted in any position.

In particular the present invention provides an azepinoindole of formula I,

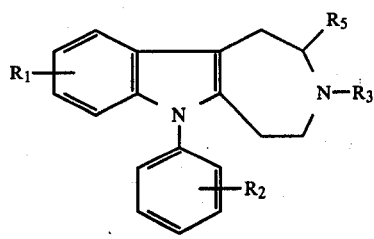

wherein $R_1$ and $R_2$ are each independently hydrogen, halogen of atomic number from 9 to 35, $(C_{1-4})$alkyl, $(C_{1-4})$alkoxy, $(C_{1-4})$alkylthio, hydroxy, or trifluoromethyl, $R_3$ is hydrogen, $(C_{1-4})$alkyl, $(C_{3-6})$cycloalkyl, $(C_{4-9})$cycloalkylalkyl, $(C_{3-5})$alkenyl, $(C_{3-5})$alkinyl, a group of formula II,

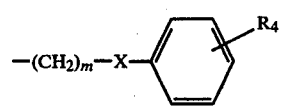

wherein m is 1, 2 or 3, $R_4$ is halogen of atomic number from 9 to 35, $(C_{1-4})$alkyl, $(C_{1-4})$alkoxy, or trifluoromethyl, and X is a bond, —CHOH— or —CH—, or a group of formula III,

wherein n is 2 or 3, and $R_5$ is hydrogen or $(C_{1-4})$alkyl.

In formula I $R_1$ is preferably in position 8 or 9 of the nucleus. $R_2$ is preferably in the para position of the phenyl ring. Halogen is preferably chlorine or fluorine and especially fluorine. Alkyl, alkylthio, and alkoxy have preferably 1 or 2 carbon atoms, and especially 1 carbon atom. Alkenyl and alkinyl preferably have 3 or 4 carbon atoms, especially 3 carbon atoms. m is preferably 2 or 3. When $R_3$ is a radical of formula II, $R_4$ is preferably in the ortho or para position of the phenyl ring.

The present invention in another aspect provides a process for the production of a compound of the invention which comprises (i) treating a 1,2,3,4-tetrahydro-9-phenylpyrido[3,4-b]indole having a chloromethyl or bromomethyl group in the 1 position and unsubstituted on the nitrogen atom in the 2 position, with a complex hydride to obtain a 1,2,3,4,5,6-hexahydro-6-phenyl-azepino[4,5-b]indole unsubstituted on the nitrogen atom in the 3 position, and, optionally, (ii) interconverting the 1,2,3,4,5,6-hexahydro-6-phenyl-azepino[4,5-b]indole into another 1,2,3,4,5,6-hexahydro-6-phenyl-azepino[4,5-b]indole, e.g. by alkylating the amino group in the 3 position or splitting any ring alkoxy groups to produce hydroxy groups.

In particular a compound of formula I as defined above may be produced by a process which comprises (a) obtaining a compound of formula Ia,

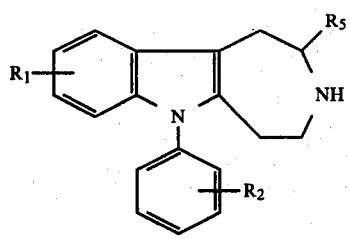

wherein $R_1$, $R_2$ and $R_5$ are as defined above, by enlarging the six-membered nitrogen containing ring of a compound of formula IV,

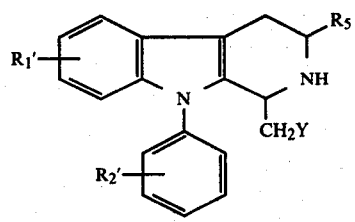

wherein $R_5$ is as defined above, and $R_1'$ and $R_2'$ have the same significance as $R_1$ and $R_2$ except that any hydroxy group present is protected by a hydrogenolytically splittable group, and Y is chlorine or bromine, and when at least one of $R_1'$ and $R_2'$ is a hydroxy group protected by a hydrogenolytically splittable group, hydrogenating the resulting compound of formula V,

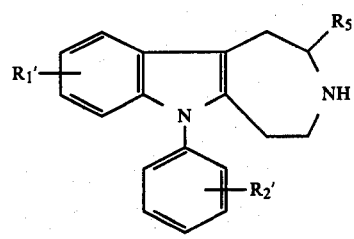

(b) obtaining a compound of formula Ib,

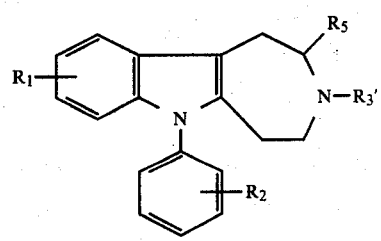

wherein

R$_1$, R$_2$ and R$_5$ are as defined above, and

R$_3'$ is as R$_3$ with the exception of hydrogen, by introducing the group R$_3'$ into a compound of formula V as defined above, and when at least one of R$_1'$ and R$_2'$ is a hydroxy group protected by a hydrogenolytically splittable group, hydrogenating the resulting compound of formula VI,

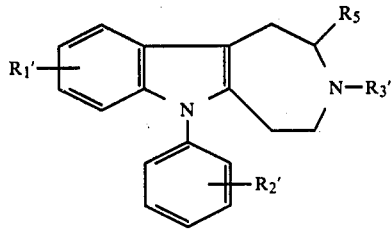

or (c) obtaining a compound of formula Ic,

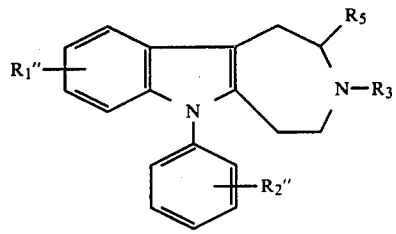

wherein

R$_1''$ and R$_2''$ have the same significances as R$_1$ and R$_2$ with the proviso that (i) none of them is an alkoxy group and (ii) at least one of them is a hydroxy group, and R$_3$ and R$_5$ are as defined above, with the proviso that, when R$_3$ is a group of formula II, R$_4$ is other than alkoxy, by subjecting a compound of formula VII,

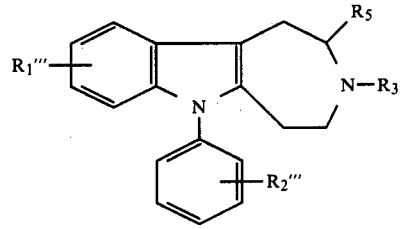

wherein

R$_1'''$ and R$_2'''$ have the same significances as R$_1$ and R$_2$ with the proviso that at least one of them is alkoxy, R$_3$ and R$_5$ are as defined above, with the proviso that when R$_3$ is a group of formula II, R$_4$ is other than alkoxy, to an ether splitting.

Process (i) or (a) is conveniently effected in an inert organic solvent, e.g. a cyclic or aliphatic ether, preferably dioxane or tetrahydrofuran. Suitable temperatures are from about 20° C. to the reflux temperature, preferably about 60° C. The complex hydride is conveniently aluminium hydride, sodium borohydride or lithium aluminium hydride. When at least one of R$_1$ and R$_2$ is chlorine, it is preferred to use aluminium hydride or sodium borohydride.

Benzyloxy is used as the preferred protected hydroxy group.

The splitting off of the protecting group in formula V may be effected in conventional manner, e.g. by catalytic hydrogenation using a palladium catalyst.

The catalytic hydrogenation may be effected in an appropriate solvent, e.g. ethanol. Suitable temperatures are from about 0° C. to about 40° C.

The alkylation reaction of process (b) may be effected in conventional manner for the alkylation of an analogous secondary ring amine. As alkylating agent may be used reactive derivatives of a compound of formula R$_3'$OH, e.g. a halide ester or a sulphuric acid derivative. When R$_3'$ is an alkyl group or a substituted alkyl group such as cycloalkylalkyl, wherein the α-carbon atom bears a hydrogen atom, then an appropriate aldehyde or ketone may be used in the presence of an appropriate reducing agent, e.g. formic acid.

The catalytic reduction may be effected in analogous manner to that mentioned above.

The process according to reaction (c) may be effected in conventional manner for an ether splitting to form hydroxy groups. The reaction may be effected using for example hydrogen iodide, hydrogen bromide, hydrogen chloride. Suitable temperatures are from room temperatures to about 100° C. An organic solvent such as acetic acid may be present. Additionally borontribromide may be used as the ether splitting agent. Suitable temperatures are from about −60° C. to room temperature. Dichloromethane may be used as organic solvent.

A starting material of formula IV may by obtained for example by as follows:

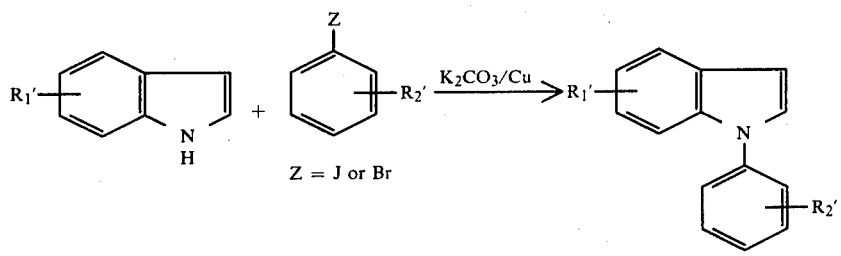

POCl$_3$/DMF (Vilsmeyer reaction)

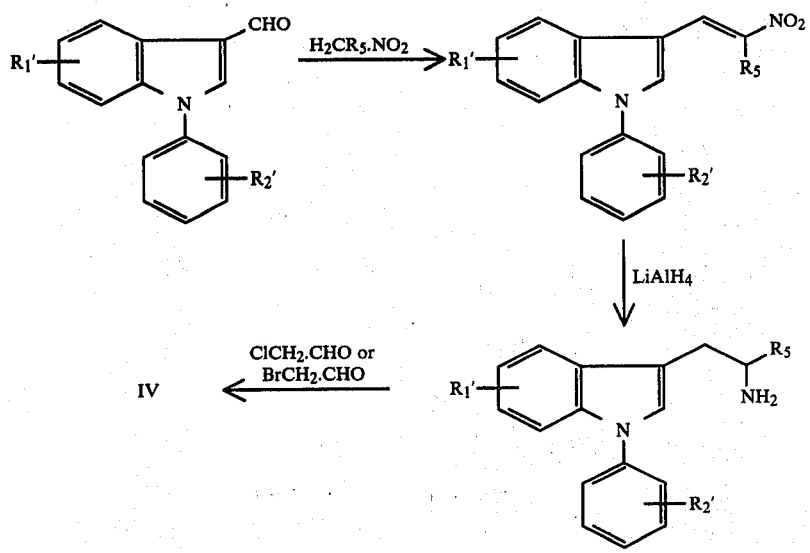

Insofar as the preparation of any particular starting material is not particularly described, this is known or may be made in known manner or in a manner analogous to the processes described herein.

Free base forms of the compounds of the invention may be converted into acid addition salt forms in conventional manner and vice versa. Suitable acids for salt formation include hydrochloric acid, fumaric acid, oxalic acid.

In the following Examples all temperatures are in degrees Centigrade and are uncorrected.

In the table the following abbreviations are used:
(1) hydrochloride
(2) hydrogen fumarate
(3) hydrogen oxalate
(4) decomposition
(5) oxalate

EXAMPLE 1

1,2,3,4,5,6-Hexahydro-6-phenylazepino[4,5-b]indole (process a)

A cold solution of 9.5 ml sulphuric acid monohydrate in 200 ml tetrahydrofuran is added dropwise to a suspension of 35.6 g lithium aluminium hydride in 1500 ml tetrahydrofuran at −10°. The mixture is warmed to 60° and a suspension of 79.2 g 1-chloromethyl-1,2,3,4-tetrahydro-9-phenylpyrido[3,4-b]indole hydrochloride in 200 ml tetrahydrofuran is added dropwise. The mixture is then warmed for a further 45 minutes, cooled to 0° and the reaction mixture treated dropwise with a saturated sodium sulphate solution. The precipitate is filtered off and washed with ether. The filtrates are concentrated at reduced pressure, and the title compound crystallizes out, m.p. 108°–111° (from ether/pentane). M.p. hydrochloride 220°–224° (from ethanol/ether).

The starting material 1-chloromethyl-1,2,3,4-tetrahydro-9-phenylpyrido[3,4-b]indole may be obtained as follows:

(a) 120 g 1-phenylindole-3-carboxaldehyde and 16.2 g ammonium acetate are heated under reflux in 406 ml nitromethane for 5 hours. The mixture is cooled, diluted with ether to give 3-(2-nitroethenyl)-1-phenylindole, m.p. 154°–155°.

(b) A suspension of 109.2 g 3-(2-nitroethenyl)-1-phenylindole in 990 ml tetrahydrofuran is added dropwise at 20° to 43.5 g lithium aluminium hydride in 570 ml tetrahydrofuran. The mixture is heated at 60° for 20 minutes. The reaction mixture is cooled. A saturated sodium sulphate solution is added dropwise at −10° C. The mixture is filtered and the precipitate washed with ether. The filtrate is concentrated and the residue, 3-(2-aminoethyl)-1-phenylindole, is converted into the hydrochloride, m.p. 216°–220° (from ethanol/ether).

(c) 55.6 ml chloroacetaldehyde (45% in water) are added dropwise to 87.2 g 3-(2-aminoethyl)-1-phenylindole, 400 ml 2N hydrochloric acid and 2.5 liters water at 50°. The mixture is heated for 1 hour at 95°, treated once more with 55.6 ml chloroacetaldehyde and heated for a further 45 minutes. The mixture is then cooled to 0°, made alkaline with conc. ammonia and shaken with ether. The organic phase is dried over sodium sulphate, and purified with animal charcoal, and concentrated. The residue 1-chloromethyl-1,2,3,4-tetrahydro-9-phenylpyrido[3,4-b]indole is converted into the hydrochloride, m.p. 174°–180° (from ethanol/ether).

EXAMPLE 2

1,2,3,4,5,6-Hexahydro-3-methyl-6-phenylazepino[4,5-b]indole (process b)

19.8 ml of a 35% formaldehyde solution and a spoonful of Raney Nickel are added to 20.4 g 1,2,3,4,5,6-hexahydro-6-phenylazepino[4,5-b]indole in 385 ml ethanol. The mixture is hydrogenated at room temperature. The mixture is then filtered and the filtrate concentrated to give a residue which is partitioned between ether and water. The ether phase is dried over sodium sulphate and concentrated to give the title compound as an oil which is converted into the hydrochloride, m.p. 236°–238° (from ether/ethanol).

EXAMPLE 3

3-Allyl-9-fluoro-6-p-fluorophenyl-1,2,3,4,5,6-hexahydro-azepino[4,5-b]indole 3.1 ml allyl bromide are added dropwise to 9.0 g of 9-fluoro-6-p-fluorophenyl-1,2,3,4,5,6-hexahydro-azepino[4,5-b]indole and 9 g potassium carbonate in 90 ml dimethylformamide. The mixture is stirred for 2 hours at 110° C., cooled to room temperature, poured onto water, and extracted with ether. The ether extracts are concentrated to give the title compound as a residue. M.p. of the hydrochloride 228°–228° (decomp.).

EXAMPLE 4

9-Fluoro-6-p-fluorophenyl-1,2,3,4,5,6-hexahydro-3-methyl-azepino[4,5-b]indole 8.7 ml of a 35% formaldehyde solution are added dropwise to a solution of 9 g of 9-fluoro-6-p-fluorophenyl-1,2,3,4,5,6-hexahydro-azepino[4,5-b]indole in 6.9 g of formic acid. The mixture is heated for 10 minutes to 70°, cooled, poured onto water, made alkaline with concentrated ammonia and extracted with ether. The ether extracts are dried over sodium sulphate and concentrated to give the title compound in hydrochloride form, m.p. 215° (decomp.; from ether/acetone).

EXAMPLE 5

1,2,3,4,5,6-Hexahydro-9-hydroxy-3-methyl-6-phenylazepino[4,5-b]indole (process c)

A solution of 3.58 g of boron tribromide in 10 ml dichloromethane is added dropwise at −60° to a solution of 2 g 1,2,3,4,5,6-hexahydro-9-methoxy-3-methyl-6-phenyl-azepino[4,5-b]indole in 20 ml dichloromethane. The mixture is stirred at −60° for 1 hour and a dark oil separates out. The mixture is concentrated under reduced pressure and the residual oil is treated with 30 ml ethanol. The mixture is brought to reflux over 30 minutes and the hydrobromide of the title compound crystallizes out. The salt is then filtered off, washed with a little alcohol and partitioned between dichloromethane and aqueous ammonia to form the free base. The organic phase is separated off, washed with water, dried over sodium sulphate, filtered and concentrated under reduced pressure. The oily residue is dissolved in alcohol, treated with hydrochloric acid in ethanol to form the title compound in hydrochloride form, m.p. 290°–292° (decomp.).

The following compounds of formula I are produced wherein:

| Ex. | $R_1$ | $R_2$ | $R_3$ | $R_5$ | m.p. | Analogous to Ex. |
|---|---|---|---|---|---|---|
| 6 | 9-CH$_3$ | p-CH$_3$ | H | H | 242[1] | 1 |
| 7 | 9-F | p-F | H | H | 198–205[1] | 1 |
| 8 | 10-Cl | H | H | H | 136–138 | 1 |
| 9 | 9-Cl | H | H | H | 128–130 | 1 |
| 10 | 8-Cl | H | H | H | oil | 1 |
| 11 | 9-OCH$_3$ | H | H | H | oil | 1 |
| 12 | 9-Cl | p-F | H | H | oil | 1 |
| 13 | 9-Cl | p-Cl | H | H | oil | 1 |
| 14 | H | H | H | CH$_3$ | oil | 1 |
| 15 | 9-Cl | p-F | H | CH$_3$ | oil | 1 |
| 16 | 9-CH$_3$ | p-CH$_3$ | CH$_3$ | H | 270[1][4] | 2, 4 |
| 17 | 10-Cl | H | CH$_3$ | H | 282[1][4] | 4 |
| 18 | 9-Cl | H | CH$_3$ | H | 258–260[1][4] | 4 |
| 19 | 8-Cl | H | CH$_3$ | H | 273[1][4] | 4 |
| 20 | 9-F | p-F | CH$_3$ | H | 285–287[1] | 4 |
| 21 | H | H | —CH$_2$—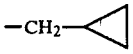 | H | 207–210[1] | 2, 3, 4 |
| 22 | 9-OCH$_3$ | H | CH$_3$ | H | 251–252[1] | 2, 4 |
| 23 | 9-Cl | p-F | CH$_3$ | H | 294–296[1][4] | 4 |
| 24 | 9-Cl | p-Cl | CH$_3$ | H | 260–262[1][4] | 4 |
| 25 | H | H | CH$_3$ | CH$_3$ | 203–206[2] | 2, 4 |
| 26 | 9-Cl | p-F | CH$_3$ | CH$_3$ | 268–270[1] | 4 |
| 27 | 9-F | p-F | —(CH$_2$)$_3$COC$_6$H$_4$—pF | H | 195–198[2] | 3 |
| 28 | 9-F | p-F | —(CH$_2$)$_3$CH(OH)C$_6$H$_4$—pF | H | 193–194[2] | 3 |
| 29 | 9-CH$_3$ | p-CH$_3$ | —(CH$_2$—CH$_2$—O)$_3$H | H | 123–126[3] | 3 |
| 30 | 9-CH$_3$ | p-CH$_3$ | —(CH$_2$—CH$_2$—O)$_2$H | H | 125–127[5] | 3 |
| 31 | H | H | 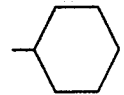 | H | 193–196[2][4] | 3 |
| 32 | H | m-SCH$_3$ | CH$_3$ | H | | 2,4 |
| 33 | 7-Cl | H | CH$_3$ | H | | 4 |
| 34 | 7-OCH$_3$ | H | CH$_3$ | H | | 2, 4 |
| 35 | 8-OH | H | CH$_3$ | H | | 5 |
| 36 | 9-Cl | m-Cl | CH$_3$ | H | | 4 |
| 37 | 8-Cl | p-Cl | CH$_3$ | H | | 4 |
| 38 | 7-Cl | H | H | H | | 1 |
| 39 | 8-OCH$_3$ | H | H | H | | 1 |
| 40 | 9-Cl | m-Cl | H | H | | 1 |
| 41 | 8-Cl | p-Cl | H | H | | 1 |
| 42 | H | H | C$_2$H$_5$ | H | 205–211[1] | 3 |
| 43 | 9-F | p-F | (CH$_2$)$_2$C$_6$H$_4$—oCl | H | 185–190[1] | 3 |
| 44 | 9-CH$_3$ | p-CH$_3$ | (CH$_2$)$_3$COC$_6$H$_4$—pF | H | 175–182[1] | 3 |

For Examples 10 to 15 Rf-values following thin layer chromatography [dichloromethane/ethanol/25% ammonia (90:9:1)]:
Examples 10–13: Rf = 0.3
Examples 14 and 15: Rf = 0.45

In analogous manner to that disclosed in Example 3 the following compounds of formula I may be prepared wherein $R_5$ is iso-$C_4H_9$ and $R_1$, $R_2$ and $R_3$ are defined as follows:

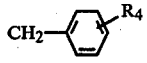

| Ex. | $R_1$ | $R_2$ | $R_3$ |
|---|---|---|---|
| (a) | 7-$SC_2H_5$ | O—$OC_2H_5$ | $C_2H_4$—CH=$CH_2$ |
| (b) | 7-$CF_3$ | m-$SC_2H_5$ | $CH_2$—C≡CH |
| (c) | 7-OH | p-OH | —◁ |
| (d) | 7-$CF_3$ | p-$CF_3$ | $CH_2$—⟨⟩—$R_4$ $R_4$ = 4-$C_2H_5$, 2-$OC_2H_5$ or 3-$CF_3$ |
| (e) | 7-$CF_3$ | p-$CF_3$ | —$(CH_2$—$CH_2$—$O)_n$H $n = 2$ or $3$ |

The compounds of the invention possess pharmacological activity in animals and are therefore useful as pharmaceuticals, e.g. for therapy. In particular, the compounds of the invention are useful as neuroleptic agents in the treatment of e.g. psychotic disturbances such as schizophrenia, as indicated in standard tests, e.g. by an inhibition of spontaneous motor activity in mice on p.o. administration of from about 1 to about 50 mg/kg animal body weight of the compounds in accordance with the principles of Caviezel and Baillod (Pharm. Acta Helv. (1958), 33, 465–484). Additionally, the compounds on administration to mice of from about 0.1 to about 10 mg/kg i.p. inhibit the hypermotility induced by 4,α-dimethyl-m-tyramine (H 77/77) in a test carried out according to the principles of C. Rüdeberg, Psychopharmacology, 59, 247–254, (1978). The compounds also increase the sleep phase II in the sleep/-wake cycle in the rat on administration of from 2 to 20 mg p.o.

For the above mentioned use the dosage will, of course, vary depending on the compound employed, mode of administration and therapy desired. However, in general, satisfactory results are obtained with a daily dosage of from about 0.2 mg to about 100 mg per kg animal body weight, conveniently given in divided doses 2 to 4 times a day or in sustained release form. For the larger mammals, the total daily dosage is in the range from about 25 mg to about 100 mg, and dosage forms suitable for oral administration comprise from about 6 mg to about 50 mg of the compounds admixed with a solid or liquid pharmaceutical carrier or diluent.

The compounds of the invention are further useful as anti-depressant agents as indicated in standard tests, for example, by an inhibition of tetrabenazine-induced catalepsy and ptosis in rats on intraperitoneal administration of from 1 to 50 mg per kilogram animal body weight of the compound in accordance with the method described by Stille (Arzneimittel-Forschung 1964, 14, 534).

For the above-mentioned use the dosage will, of course, vary depending on the compound employed, mode of administration and condition to be treated. However, in general, satisfactory results are obtained with a daily dosage of from about 0.05 to about 50 mg per kg animal body weight, preferably given in divided doses 2 to 4 times a day, or in sustained release form. For the larger mammals the total daily dosage is in the range from about 20 to about 100 mg and dosage forms suitable for oral administration comprise from about 5 to about 50 mg of the compound admixed with a solid or liquid pharmaceutical carrier or diluent.

Additionally the compounds of the invention are useful for the prophylaxis and therapy of allergic conditions, e.g. allergic and exercise-induced asthma, rhinitis, conjuctivitis, uriticaria, allergic conditions of the gastro-intestinal-tract and food allergies, on the skin, lung or in the form of migraine, as indicated in standard tests. For example, according to the principles of J. Mota, Immunology, 7, 681, (1964), in the passive cutaneous anaphylaxis test (PCA test) in the rat, the compounds are active in a dose of from about 0.1 to about 3.2 mg/kg p.o.

For the above-mentioned use the dosage will, of course, vary depending on the compound employed, mode of administration and therapy desired. However, in general, satisfactory results are obtained with a daily dosage of from 0.007 mg to about 5 mg per kg animal body weight, conveniently in divided doses 2 to 4 times a day or in sustained release form. For the larger mammals, the total daily dosage is in the range from about 0.5 to about 10 mg, and dosage forms suitable for oral administration contain from about 0.12 to about 5 mg of the compound.

The compounds of the invention may be administered in pharmaceutically acceptable acid addition salt form. Such acid addition salt forms exhibit the same order of activity as the free base forms. The present invention also provides a pharmaceutical composition comprising a compound of the invention, in free base form, or in pharmaceutically acceptable acid addition salt form, in association with a pharmaceutical carrier or diluent. Such composition may be in the form of, for example, a solution or a tablet.

The neuroleptic activity is the preferred utility. The preferred compound is the Example 2 compound.

One group of compounds comprises compounds of formula I wherein $R_1$ and $R_2$ are independently hydrogen, halogen of atomic number from 9 to 35, ($C_{1-4}$)alkyl, ($C_{1-4}$)alkoxy, hydroxy or trifluoromethyl, $R_3$ is hydrogen, ($C_{1-4}$)alkyl, ($C_{3-5}$)alkenyl, ($C_{3-5}$)alkinyl, or a group of formula II as defined above wherein either m is 3, X is CO and $R_4$ is fluorine in the para position or m is 1 or 2, X is a bond and $R_4$ is halogen of atomic number from 9 to 35, ($C_{1-4}$)alkyl, ($C_{1-4}$)alkoxy, or trifluoromethyl, and $R_5$ is hydrogen, with the proviso that, when one of $R_1$ and $R_2$ is hydroxy, the other is hydrogen, halogen of atomic number from 9 to 35, ($C_{1-4}$)alkyl, hydroxy or trifluoromethyl.

The compound of Example 2 has been found to be active at e.g. about 10 mg/kg p.o. in neuroleptic tests as mentioned above.

In a 1st group of compounds $R_3$ is H.
In a 2nd group of compounds $R_3$ is alkyl.
In a 3rd group of compounds $R_3$ is alkenyl.
In a 4th group of compounds $R_3$ is alkinyl.
In a 5th group of compounds $R_3$ is cycloalkyl.
In a 6th group of compounds $R_3$ is cycloalkylalkyl.
In a 7th group of compounds $R_3$ is a group of formula II.
In a 8th group of compounds X is a bond.
In a 9th group of compounds X is CHOH.
In a 10th group of compounds X is CO.
In a 11th group of compounds $R_4$ is halogen.
In a 12th group of compounds $R_4$ is alkyl.
In a 13th group of compounds $R_4$ is alkoxy.
In a 14th group of compounds $R_5$ is alkyl.

In a 15th group of compounds $R_3$ is a group of formula III.

What we claim is:

1. An azepinoindole of formula I,

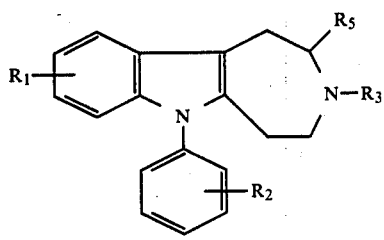

wherein $R_1$ and $R_2$ are each independently hydrogen, halogen of atomic number from 9 to 35, $(C_{1-4})$alkyl, $(C_{1-4})$alkoxy, $(C_{1-4})$alkylthio, hydroxy, or trifluoromethyl, $R_3$ is hydrogen, $(C_{1-4})$alkyl, $(C_{3-6})$cycloalkyl, $(C_{4-9})$cycloalkylalkyl, $(C_{3-5})$alkenyl, $(C_{3-5}$alkynyl, a group of formula II,

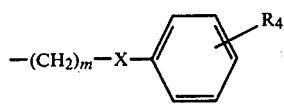

wherein m is 1, 2 or 3, $R_4$ is halogen of atomic number from 9 to 35, $(C_{1-4})$alkyl, $(C_{1-4})$alkoxy, or trifluoromethyl, and X is a bond, —CHOH— or —CO—, or a group of formula III,

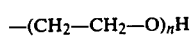

wherein n is 2 or 3, and $R_5$ is hydrogen or $(C_{1-4})$alkyl, said compound being in free base or in pharmaceutically acceptable acid addition salt form.

2. A compound of claim 1 wherein $R_1$ and $R_2$ are, independently, hydrogen, halogen of atomic number from 9 to 35, $(C_{1-4})$alkyl, $(C_{1-4})$alkoxy, hydroxy or trifluoromethyl; $R_3$ is hydrogen $(C_{1-4})$alkyl, $(C_{3-5})$alkenyl, $(C_{3-5})$alkynyl or a group of formula II wherein either m is 3, X is CO and $R_4$ is fluorine in the para position or m is 1 or 2, X is a bond and $R_4$ is halogen of atomic number from 9 to 35, $(C_{1-4})$alkyl, $(C_{1-4})$alkoxy or trifluoromethyl; and $R_5$ is hydrogen, with the proviso that, when one of $R_1$ and $R_2$ is hydroxy, the other is hydrogen, halogen of atomic number from 9 to 35, $(C_{1-4})$alkyl, hydroxy or trifluoromethyl, said compound being in free base or in pharmaceutically acceptable acid addition salt form.

3. A compound of claim 1 wherein $R_5$ is $(C_{1-4})$alkyl, said compound being in free base or in pharmaceutically acceptable acid addition salt form.

4. A compound of claim 1 wherein when $R_1$ is other than hydrogen, it is in the 8- or 9-position of the azepinoindole nucleus, said compound being in free base or in pharmaceutically acceptable acid addition salt form.

5. A compound of claim 1 where when $R_2$ is other than hydrogen, it is in the para position of the phenyl ring, said compound being in free base or in pharmaceutically acceptable acid addition salt form.

6. A compound of claim 1 wherein $R_3$ is $(C_{1-4})$alkyl, said compound being in free base or in pharmaceutically acceptable acid addition salt form.

7. A compound of claim 1 which is 1,2,3,4,5,6-hexahydro-3-methyl-6-phenyl-azepino[4,5-b]indole.

* * * * *